US009856200B2

(12) United States Patent
Karim et al.

(10) Patent No.: US 9,856,200 B2
(45) Date of Patent: *Jan. 2, 2018

(54) SUPPORTED CATALYST FOR PRODUCTION OF UNSATURATED CARBOXYLIC ACIDS FROM ALKANES

(71) Applicant: SAUDI BASIC INDUSTRIES CORPORATION, Riyadh (SA)

(72) Inventors: Khalid Karim, Riyadh (SA); Abdulaziz Al Jodai, Riyadh (SA)

(73) Assignee: Saudi Basic Industries Corporation, Riyadh (SA)

(*) Notice: Subject to any disclaimer, the term of this patent is extended or adjusted under 35 U.S.C. 154(b) by 0 days.

This patent is subject to a terminal disclaimer.

(21) Appl. No.: 14/786,000

(22) PCT Filed: Apr. 22, 2014

(86) PCT No.: PCT/IB2014/001399
§ 371 (c)(1),
(2) Date: Oct. 21, 2015

(87) PCT Pub. No.: WO2014/174371
PCT Pub. Date: Oct. 30, 2014

(65) Prior Publication Data
US 2016/0068462 A1 Mar. 10, 2016

Related U.S. Application Data

(60) Provisional application No. 61/815,435, filed on Apr. 24, 2013.

(51) Int. Cl.
B01J 27/057 (2006.01)
B01J 37/04 (2006.01)
(Continued)

(52) U.S. Cl.
CPC ......... C07C 51/215 (2013.01); B01J 23/6525 (2013.01); B01J 27/0576 (2013.01);
(Continued)

(58) Field of Classification Search
None
See application file for complete search history.

(56) References Cited

U.S. PATENT DOCUMENTS 3,098,102 A 7/1963 Bethell et al.
3,775,474 A 11/1973 Ohara et al.
(Continued)

FOREIGN PATENT DOCUMENTS

CN 1326378 A 12/2001
CN 1830556 A 9/2006
(Continued)

OTHER PUBLICATIONS

Guliants, V.V. et al., Mesoporous and Nanostructured Multicomponent Mo—V—Te—Nb—O Catalysts for Propane Ammoxidation to Acrylonitrile, AIChE Annual Meeting, Conference Proceedings (2006).
(Continued)

Primary Examiner — Colin W. Slifka
(74) Attorney, Agent, or Firm — Ballard Spahr LLP

(57) ABSTRACT

The present disclosures and inventions relate to a supported catalyst composition for the catalytic oxidation of a hydrocarbon such as propane with oxygen or air, in the presence of a catalyst composition comprising a support material and a mixed metal composition comprising metals in the molar ratios described by the formula $Mo_aV_bGa_cPd_dNb_eZ_f$, wherein the support material is neutral or oxidative.

20 Claims, 1 Drawing Sheet

(51) Int. Cl.
    *C07C 51/215*     (2006.01)
    *B01J 23/652*     (2006.01)
    *C07C 5/48*     (2006.01)

(52) U.S. Cl.
    CPC ............... *B01J 37/04* (2013.01); *C07C 5/48* (2013.01); *B01J 2523/00* (2013.01); *C07C 2527/057* (2013.01); *Y02P 20/582* (2015.11)

(56) References Cited

U.S. PATENT DOCUMENTS

| | | | |
|---|---|---|---|
| 4,035,262 | A | 7/1977 | Childress et al. |
| 6,114,278 | A | 9/2000 | Karim et al. |
| 6,160,162 | A | 12/2000 | Karim et al. |
| 6,258,992 | B1 * | 7/2001 | Karim .............. C07C 51/215 560/245 |
| 6,646,158 | B1 | 11/2003 | Khan et al. |
| 6,906,208 | B2 | 6/2005 | Shan et al. |
| 7,285,514 | B2 | 10/2007 | Kang et al. |
| 9,636,663 | B2 | 5/2017 | Karim et al. |
| 2002/0115879 | A1 | 8/2002 | Hinago et al. |
| 2003/0088118 | A1 | 5/2003 | Komada et al. |
| 2003/0208085 | A1 | 11/2003 | Gaffney et al. |
| 2004/0030184 | A1 | 2/2004 | Cook et al. |
| 2005/0054869 | A1 | 3/2005 | Lugmair et al. |
| 2005/0131255 | A1 | 6/2005 | Benderly et al. |
| 2005/0202965 | A1 | 9/2005 | Cavalcanti et al. |
| 2005/0228196 | A1 | 10/2005 | Gaffney et al. |
| 2006/0047137 | A1 | 3/2006 | Tu et al. |
| 2006/0183941 | A1 | 8/2006 | Dubois et al. |
| 2006/0205978 | A1 | 9/2006 | Yunoki et al. |
| 2006/0235238 | A1 | 10/2006 | Komada et al. |
| 2006/0293538 | A1 | 12/2006 | Dubois et al. |
| 2007/0161767 | A1 | 7/2007 | Tu et al. |
| 2008/0139844 | A1 | 6/2008 | Dubois et al. |
| 2008/0194871 | A1 | 8/2008 | Dubois et al. |
| 2012/0071571 | A1 * | 3/2012 | Abbas ............... B01J 23/8896 518/700 |

FOREIGN PATENT DOCUMENTS

| | | |
|---|---|---|
| CN | 1830938 | 9/2006 |
| EP | 1318127 A2 | 6/2003 |
| EP | 1521633 A1 | 4/2005 |
| EP | 1533029 A1 | 5/2005 |
| EP | 1574254 A2 | 9/2005 |
| EP | 1806178 A1 | 7/2007 |
| GB | 1353864 A | 5/1974 |
| JP | 2001-347165 A | 12/2001 |
| JP | 2004-041839 A | 2/2004 |
| JP | 2004-041880 A | 2/2004 |
| JP | 2004-066024 A | 3/2004 |
| JP | 2004-188341 A | 7/2004 |
| JP | 2005-074377 A | 3/2005 |
| WO | WO00/29106 * | 5/2000 |
| WO | WO-00/29106 A1 | 5/2000 |
| WO | WO-0183103 A2 | 11/2001 |
| WO | WO-2004/007071 A1 | 1/2004 |
| WO | WO-2006/058998 A2 | 6/2006 |
| WO | WO-2008/068332 A1 | 6/2008 |
| WO | WO-2008/152952 A1 | 12/2008 |
| WO | WO-2014/174375 A2 | 10/2014 |

OTHER PUBLICATIONS

Herbet, R. et al., Nanostructured Vanadium Oxide Model Catalysts Based on Mesoporous SBA-15, Chemie-Ingenieur-Technik, 78(9): 1263 (2006).
Hess, C., Direct Correlation of the Dispersion and Structure in Vanadium Oxide Supported on Silica SBA-15, J Catalysis, 248(1): 120 (2007).
Hess, C., Nanostructured Vanadium Oxide Model Catalysts for Selective Oxidation Reactions, Chemphyschem, 10(2): 319 (2009).
International Search Report dated Jan. 29, 2015 by the International Searching Authority for International Patent Application No. PCT/162014/001432, which was filed on Apr. 22, 2014 and published as WO 2014/175375 (Inventor—Karim et al.; Applicant—Saudi Basic Industries Corp.) (5 pages).
International Search Report dated Dec. 1, 2014 by the International Searching Authority for International Patent Application No. PCT/IB2014/001399, which was filed on Apr. 22, 2014 and published as WO 2014/174371 on Oct. 30, 2014 (Inventor—Karim et al; Applicant Saudi Basic Industries Corp.) (5 pages).
Written Opinion dated Oct. 24, 2015 by the International Searching Authority for International Application No. PCT/IB2014/001432, which was filed on Apr. 22, 2014 and published as WO/2014/174375 on Oct. 30, 2014 (Applicant-Saudi Basic Industries Corporation) (5 pages).
International Preliminary Report on Patentability dated Oct. 24, 2015 by the International Searching Authority for International Application No. PCT/IB2014/001432, which was filed on Apr. 22, 2014 and published as WO/2014/174375 on Oct. 30, 2014 (Applicant—Saudi Basic Industries Corporation) (6 pages).
Written Opinion dated Oct. 24, 2015 by the International Searching Authority for International Application No. PCT/IB2014/001399, which was filed on Apr. 22, 2014 and published as WO2014/174371 on Oct. 30, 2014 (Applicant—Saudi Basic Industries Corporation) (4 pages).
International Preliminary Report on Patentability dated Oct. 27, 2015 by the International Searching Authority for International Application No. PCT/IB2014/001399, which was filed on Apr. 22, 2014 and published as WO2014/174371 on Oct. 30, 2014 (Applicant-Saudi Basic Industries Corporation) (5 pages).

* cited by examiner

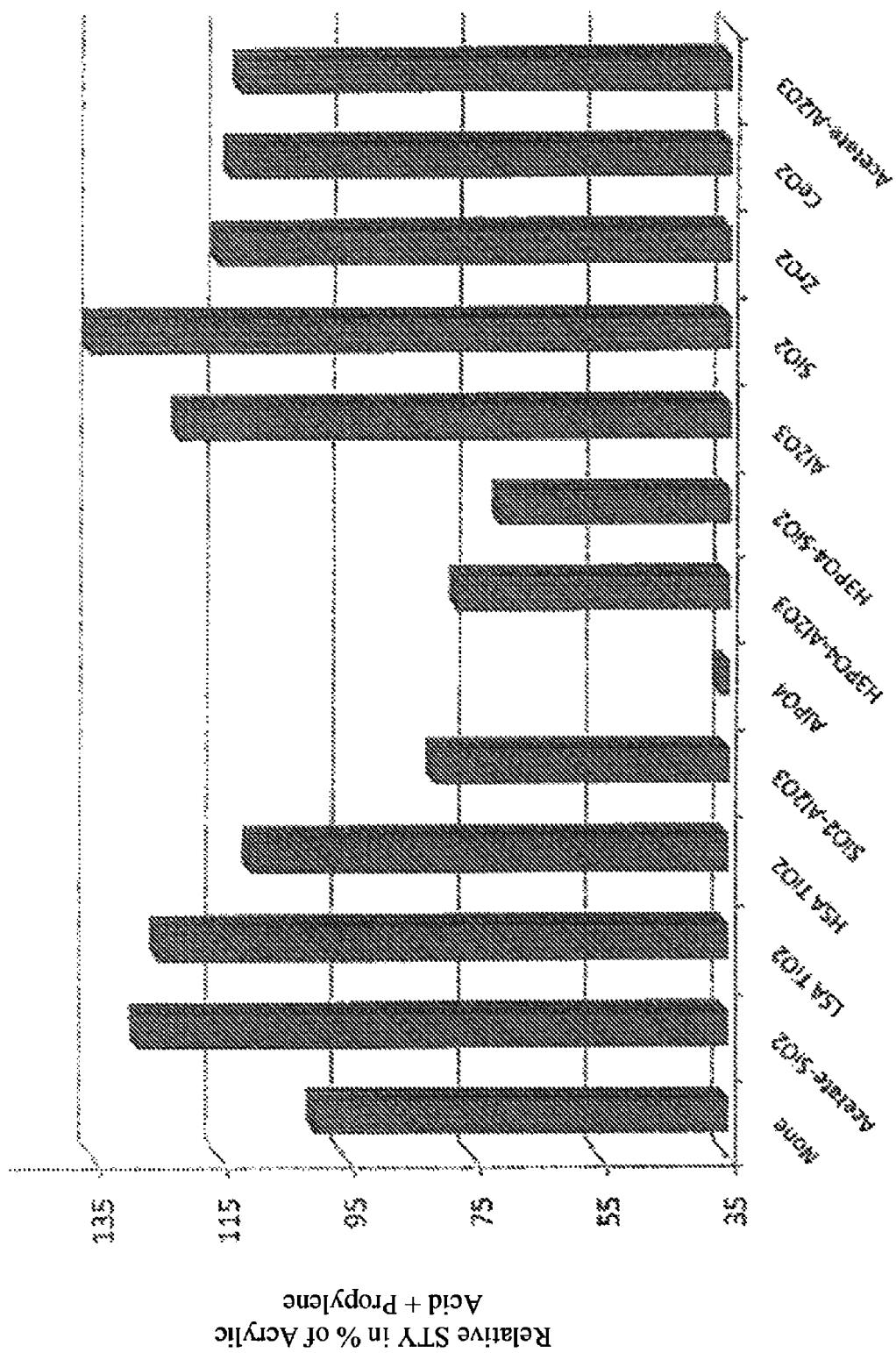

SUPPORTED CATALYST FOR PRODUCTION OF UNSATURATED CARBOXYLIC ACIDS FROM ALKANES

CROSS-REFERENCE TO RELATED APPLICATIONS

This is a U.S. National Phase Application of International Application No. PCT/IB2014/001399, filed Apr. 22, 2014, which claims the benefit of U.S. Provisional Application No. 61/815,435, filed on Apr. 24, 2013, which are both incorporated herein by reference in their entirety.

FIELD OF THE INVENTION

The present compounds, compositions, and methods relate to supported catalyst compositions for the catalytic oxidation of alkanes to α,β-unsaturated carboxylic acids and/or olefins.

BACKGROUND

Conversion of alkanes, such as propane, to more valuable materials such as α,β-unsaturated carboxylic acids and/or olefins, for example, acrylic acid and propylene is highly desired in industry. Propane and propylene are widely produced commercially from oil and natural gas via a variety of widely known processes in oil refineries. Propylene is useful for making a variety of additional downstream products via known commercial processes, and commands a significantly higher price than propane. The vapor phase oxidation of propylene to acrylic acid with air or oxygen, over supported catalysts is well-known in the art and widely commercially practiced.

Catalytic oxidation of propane to acrylic acid and propylene is economically attractive. For example, such approach is economically more attractive than one of production of acrylic acid via a process requiring propylene as a starting material, because of the significant price difference between propane and propylene as starting materials.

Accordingly, disclosed herein are catalytic compositions and methods related thereto useful in the oxidation of alkanes, such as, propane to α,β-unsaturated carboxylic acids, such as acrylic acid, and/or olefins, such as propylene.

SUMMARY OF THE INVENTIONS

In accordance with the purpose(s) of the invention, disclosed herein is a catalyst composition comprising a support material and a mixed metal composition comprising metals in the molar ratios described by the formula $$Mo_aV_bGa_cPd_dNb_eZ_f,$$

wherein a is 1,
wherein b is from 0.01 to 0.9,
wherein c is greater than 0 to 0.2,
wherein d is from 0.0000001 to 0.2,
wherein e is greater than 0 to 0.2,
wherein Z comprises La, Te, Ge, Zn, Si, In, or W, or a mixture thereof,
wherein f is greater than 0 to 0.5, and
wherein the support material is neutral or oxidative.

Also disclosed herein are methods for making the catalyst compositions of the invention comprising the step of a) mixing a support material with an active phase, thereby forming a catalyst composition, wherein the support material is neutral or oxidative, thereby forming a catalyst composition.

Also disclosed herein are methods of oxidizing a $C_2$-$C_{12}$ alkane comprising, contacting the $C_2$-$C_{12}$ alkane with an oxygen containing stream and a catalyst composition comprising a support material and a mixed metal composition comprising metals in the molar ratios described by the formula $$Mo_aV_bGa_cPd_dNb_eZ_f,$$

wherein a is 1,
wherein b is from 0.01 to 0.9,
wherein c is greater than 0 to 0.2,
wherein d is from 0.0000001 to 0.2,
wherein e is greater than 0 to 0.2,
wherein Z comprises La, Te, Ge, Zn, Si, In, or W, or a mixture thereof,
wherein f is greater than 0 to 0.5, and
wherein the support material is neutral or oxidative,
thereby oxidizing the $C_2$-$C_{12}$ alkane.

It has been unexpectedly discovered that the rate of hydrocarbon (such as alkanes, for example, propane) oxidation to form α,β-unsaturated carboxylic acids (such as acrylic acid) and olefins (such as propylene), and/or the reaction temperatures required for the catalytic methods can be unexpectedly increased.

Additional advantages will be set forth in part in the description which follows, and in part will be obvious from the description, or may be learned by practice of the aspects described below. The advantages described below will be realized and attained by means of the chemical compositions, methods, and combinations thereof particularly pointed out in the appended claims. It is to be understood that both the foregoing general description and the following detailed description are exemplary and explanatory only and are not restrictive.

DESCRIPTION OF THE FIGURES

FIG. 1 shows a bar chart of the rate data from Table 1, which describes the results of propane oxidation testing of each of the catalysts as described in Examples 1-13 at 290° C., shown as a ratio of the space time yield (STY) for the combination of acrylic acid and propane, in a ratio to the STY for the unsupported mixed metal composition catalyst described in Example 1 ($Mo_1V_{0.398}Ga_{1.0E-05}Pd_{1.90E-04}Nb_{0.125}Te_{0.23}$ without a support).

DETAILED DESCRIPTION

1. Definitions

Disclosed herein are materials, compounds, compositions, and components that can be used for, can be used in conjunction with, can be used in preparation for, or are products of the disclosed methods and compositions. It is to be understood that when combinations, subsets, interactions, groups, etc. of these materials are disclosed that while specific reference of each various individual and collective combinations and permutation of these compounds may not be explicitly disclosed, each is specifically contemplated and described herein. For example, if a catalyst component is disclosed and discussed, and a number of alternative solid state forms of that component are discussed, each and every combination and permutation of the catalyst component and the solid state forms that are possible are specifically contemplated unless specifically indicated to the contrary. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

In this specification and in the claims which follow, reference will be made to a number of terms which shall be defined to have the following meanings:

It must be noted that, as used in the specification and the appended claims, the singular forms "a," "an" and "the" include plural referents unless the context clearly dictates otherwise. Thus, for example, reference to "an aromatic compound" includes mixtures of aromatic compounds, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Many of the catalyst compositions and/or catalyst components disclosed herein are described as containing a "metal" or "metals". Examples of such "metal" components include Mo, V, Ga, Pd, Nb, and Ce, La, Te, Ge, Zn, Si, In, W, Al, Na, K, Li, etc. It should be understood that references to such "metals" in this application does NOT imply a particular valence, chemical, or physical state of those elements, or that those elements are necessarily in a zero valent state, or metallic solid physical state or alloy (although they could be in such states), but rather that the "metal" or "metals" can also be present in a compound with other elements or groups wherein the metal can be present in any energetically feasible positive oxidation state (i.e. cationic oxidation states). For example, a reference to potassium (K) as a metal could include bulk metallic potassium in a zero oxidation state, or dispersions or solutions of potassium metal, or also the cationic form $K^+$ of potassium, which may be present in either liquid or solid solutions with other elements.

The terms "active phase" and "mixed metal composition" are used interchangeably herein.

As used herein, "neutral support material" or "support material that is neutral" or the like terms refer to a material that does not influence the redox property of a catalyst. Such neutral support material only provides a desired reaction surface area for the catalyst.

As used herein, "oxidative support material" or "support material that is oxidative" or the like terms refer to a material that contributes or increases to the acid-base/redox property of a catalyst. Such oxidative support material also provides a desired reaction surface area for the catalyst.

As used herein a "reference base catalyst" or the like terms refer to a catalyst with a corresponding active phase but without a corresponding complete support material that is neutral or oxidative. Thus, a support material can be absent in a reference base catalyst. However, a support material can be present wherein the support material is not neutral or oxidative. A reference base catalyst is used under equivalent reaction conditions, i.e. oxidation conditions of propane, as the corresponding composite catalyst composition.

As used herein, the terms space time yield ("STY") refers to the tons or kg of product that is produced per unit time per volume of catalyst.

2. Supported Catalyst Compositions Useful for the Oxidation of Hydrocarbons

Disclosed herein are composite catalyst compositions useful for the oxidation of hydrocarbons, such as alkanes, for example, propane. The disclosed composite catalyst compositions can have a higher activity than a reference base catalyst. The disclosed composite catalyst compositions comprise a neutral or oxidative support material and an active phase which comprises $Mo_aV_bGa_cPd_dNb_eX_f$. The active phase disclosed herein is at least partially described in PCT Publication WO 00/029106 and U.S. Pat. No. 6,160,162 which are both hereby incorporated by reference in their entirety.

Disclosed herein a catalyst composition comprising a support material and a mixed metal composition comprising metals in the molar ratios described by the formula

$Mo_aV_bGa_cPd_dNb_eZ_f$, wherein a is 1,
wherein b is from 0.01 to 0.9,
wherein c is greater than 0 to 0.2,
wherein d is from 0.0000001 to 0.2,
wherein e is greater than 0 to 0.2,
wherein Z comprises La, Te, Ge, Zn, Si, In, or W, or a mixture thereof,
wherein f is greater than 0 to 0.5, and
wherein the support material is neutral or oxidative.

In one aspect, the support material is oxidative. In another aspect, the support material is neutral.

The mixed metal composition used as a component of the composite catalyst compositions described herein can comprise any of the mixed metal compositions disclosed herein and are at least partially described in WO 00/029106 and U.S. Pat. No. 6,160,162. The solid mixed metal compositions are themselves (alone) active for the oxidation of hydrocarbons (i.e. alkanes) such as propane, and comprise a mixture of several metals in molar ratios as described by the formula: $Mo_aV_bGa_cPd_dNb_eX_f$, wherein a is 1, wherein b is from 0.01 to 0.9, wherein c is greater than 0 to 0.2, wherein d is from 0.0000001 to 0.2, wherein e is greater than 0 to 0.2, wherein X comprises La, Te, Ge, Zn, Si, In, or W, or a mixture thereof, and wherein f is greater than 0 to 0.5. In one aspect of those mixed metal compositions, X comprises Te (tellurium) or is Te. In one aspect, b is from 0.1 to 0.9. In another aspect, b is from 0.1 to 0.5. In one aspect, c is greater than 0 to 0.001. In another one aspect, c is greater than 0 to 0.0001. In one aspect, d is from 0.0000001 to 0.01. In another aspect, d is from 0.00001 to 0.01. In one aspect, e is from 0.05 to 0.2. In another aspect, e is from 0.1 to 0.2. In one aspect, f is from 0.05 to 0.5. In another aspect, f is from 0.1 to 0.5. In one aspect, a is 1, wherein b is from 0.1 to 0.5, c is greater than 0 to 0.0001, d is from 0.00001 to 0.01, e is from 0.1 to 0.2, X is Te, and wherein f is from 0.1 to 0.5. In another aspect, f is from 0.1 to 0.5. In one aspect, a is 1, wherein b is from 0.1 to 0.5, c is greater than 0 to 0.0001, d is from 0.00001 to 0.01, e is from 0.1 to 0.2, X is Te, wherein f is from 0.1 to 0.5, and wherein the support material is oxidative. In another aspect, f is from 0.1 to 0.5. In one aspect, a is 1, wherein b is from 0.1 to 0.5, c is greater than 0 to 0.0001, d is from 0.00001 to 0.01, e is from 0.1 to 0.2, X is Te, wherein f is from 0.1 to 0.5, and wherein the support material is neutral.

In one aspect, the mixed metal composition can comprise the formula $Mo_1V_{0.398}Ga_{1.0E-05}Pd_{1.90E-04}Nb_{0.125}X_f$. In another aspect, the mixed metal composition can comprise the formula $Mo_1V_{0.398}Ga_{1.0E-05}Pd_{1.90E-04}Nb_{0.125}Te_{0.23}$. In yet another aspect, the mixed metal composition can comprise the formula $Mo_1V_{0.398}Ga_{1.0E-05}Pd_{1.90E-04}Nb_{0.125}Te_{0.23}Zn_{1.0E-05}$.

Any relative proportion of the support material and the mixed metal composition can be present in the final composite catalysts. In one aspect, the support material is present in an amount from 1% by weight to 99% by weight and the mixed metal composition is present in an amount from 99% by weight to 1% by weight. In another aspect, the support material is present in an amount from 5% by weight to 90% by weight and the mixed metal composition is present in an amount from 95% by weight to 10% by weight. In yet another aspect, the support material is present in an amount from 50% by weight to 90% by weight and the mixed metal composition is present in an amount from 50% by weight to 10% by weight. In yet another aspect, the support material is present in an amount from 20% by weight to 80% by weight and the mixed metal composition is present in an amount from 80% by weight to 20% by weight. In yet another aspect, the support material is present in an amount of 90% by weight and the mixed metal composition is present in an amount of 10% by weight. In yet another aspect, the support material is present in an amount of 30% by weight and the mixed metal composition is present in an amount of 70% by weight.

In one aspect, the support materials used to make the supported catalysts disclosed herein can be either high or low surface area support materials. In another aspect, the supported catalysts disclosed herein can be a high surface area support materials. In yet another aspect, the supported catalysts disclosed herein can be a low surface area support materials.

In one aspect, the support materials used to make the supported catalysts disclosed herein can be either microporous (pore sizes up to 2 nanometers) or mesoporous (pore sizes from 2 nanometers up to 50 nanometers).

In one aspect, the support materials used to make the supported catalysts disclosed herein include $Al_2O_3$, $SiO_2$, $CeO_2$, $TiO_2$, $ZrO_2$, or a mixture thereof. In another aspect, the support material used to make the supported catalysts disclosed herein is $CeO_2$. In yet another aspect, the support material used to make the supported catalysts disclosed herein is $Al_2O_3$. In yet another aspect, the support materials used to make the supported catalysts disclosed herein is $SiO_2$. In yet another aspect, the support materials used to make the supported catalysts disclosed herein is $ZrO_2$. In yet another aspect, the support materials used to make the supported catalysts disclosed herein is $TiO_2$. In yet another aspect, the support material comprises acetate-$SiO_2$, low surface area $TiO_2$, high surface area $TiO_2$, acetate-$Al_2O_3$, acetate-$ZrO_2$, or acetate-$CeO_2$, or a mixture thereof In one aspect, the support material does not comprise a metal. In another aspect, the support material does not comprise a metal comprising B, La, Mn, Sb, Ti, Zr, La, Fe, Cs, Au, or Ce, or a mixture thereof.

It should be understood that the mixed metal compositions disclosed herein can be mixed metal compositions, wherein the metal atoms or ions are present in the spaces between a solid lattice formed by oxide anions, which could be represented by the formula $Mo_aV_bGa_cPd_dNb_eX_fO_g$, wherein a, b, c, d, e, and f have the same definition described elsewhere herein, and g can be a broad range of numbers representing the number of oxygen atoms in the mixed metal composition, that is determined stoichiometrically.

It is to be recognized that the mixed metal compositions employed can be single phase solid materials whose composition cannot be represented by simple ratios of well-defined integers, because those solids probably contain solid state point defects (such as vacancies or interstitial atoms or ions) that can cause variations in the overall stoichiometry of the composition, a phenomenon well known to those of ordinary skill in the arts related to solid inorganic materials, especially for transition metal oxides. Accordingly, for the purposes of this disclosure, the stoichiometric composition of the catalytically active mixed metal compositions described herein are quoted in ratios of moles of the other atoms as compared to the moles of molybdenum ions or atoms in the same composition (i.e. a=1).

The composite catalyst compositions can be prepared by various methods, as further described below. The composite catalyst composition, once formed, can be ground to provide catalyst particles of a size sufficient to have physical integrity, but small enough to allow diffusion of reactants and products to the catalyst surfaces. In one aspect, the catalyst composition has a particle size from 2 μm to 500 μm or from 20 μm to 500 μm.

In one aspect, the composite catalyst composition is stable to at least 600° C. Accordingly, no leaching, boiling, or sublimation of the metals in the catalyst occurs at such temperatures.

3. Methods for Preparing the Composite Catalyst Compositions

Also disclosed herein are methods of making the composite catalyst compositions disclosed herein.

In one aspect, the methods comprise the step of:
a) mixing a support material with a mixed metal composition, thereby forming a catalyst composition, wherein the support material is neutral or oxidative, thereby forming a catalyst composition.

In one aspect, the method comprises drying the support material prior to mixing the support material with the mixed metal.

In one aspect, the method further comprises baking the catalyst composition (after formation of the supported catalyst). In another aspect, the method further comprises physically modifying the catalyst composition to form particles having a range of size from 2 µm to 500 µm or from 20 µm to 500 µm.

It should be understood that the descriptions of the various catalyst components and relevant numerical ratios described above in connection with the active catalysts themselves can be and/or are applicable in connection with the methods for making those catalysts.

The mixed metal composition can be prepared by similar methods disclosed in WO 00/029106 and U.S. Pat. No. 6,160,162. In one aspect, molybdenum is introduced into a solution in the form of ammonium salts such as ammonium paramolybdate, or as organic acid salts of molybdenum such as acetates, oxalates, mandelates, and glycolates. Other partially water soluble molybdenum compounds which can be used include molybdenum oxides, molybdic acid, and chlorides of molybdenum. In one aspect, vanadium is introduced into the solution in the form of ammonium salts such as ammonium metavanadate and ammonium decavanadate, or as organic salts of vanadium such as acetates, oxalates, and tartrates. Partially water soluble vanadium compounds such as vanadium oxides, and sulfates of vanadium can also be used. To achieve complete solubility, an effective amount of oxalic or tartaric acid can be added. In one aspect, gallium is introduced into the catalyst solution or slurry in the form of salts of gallium such as oxide, chloride, nitrate, and the like. In one aspect, palladium is introduced into the catalyst slurry in the form of Pd on activated charcoal or alumina or as a solution of salts of palladium such as acetates, chlorides, nitrates, and the like. In one aspect, niobium is used in the form of oxalates or hydrate oxides. Other sources of this metal in soluble form include compounds in which the metal is coordinated, bonded or complexed to a beta-diketonate, carboxylic acid, an amine, an alcohol, or an alkanolamine.

In one aspect of the mixed metal composition, catalysts comprising both Mo and V are prepared by the following general procedure. Aqueous solutions of vanadium and molybdenum are prepared separately. The vanadium solution is mixed with the molybdenum solution at a specified temperature and pH. The remaining required components are slowly added to the combined gel solution. After mixing, the resultant gel is dried to incipient wetness with continuous stirring. After initially drying the resultant gel mixture (for example at about 120° C. for about 16 hours), the resultant solid catalyst is heated to about 350° C. and calcined at this temperature in air (for example for about for 4 hours) to produce the desired mixed metal oxide composition.

It should also be recognized that many potential solvents and many potential organic additives could be used to form the requisite solutions, slurries, or suspensions. In many embodiments water, possibly in combination with a variety of polar organic solvents, acids, or bases, or a mixture thereof could be used to form the requisite solutions, slurries, or solutions.

Once the mixed metal composition and the support material have been separately formed, they are mixed to form the composite catalyst composition, in ratios described above.

In one aspect of the methods of making the composite catalysts, the support material is dried prior to being mixed with the metal. Furthermore, in one aspect, the steps of the method comprise baking the composite catalyst composition.

After the composite catalyst composition has been formed from the mixed metal composition and the support material, it is often physically modified by various methods well known in the art, into particles having a size from 2 µm to 1000 µm or from 20 µm to 1000 µm. In one aspect, the composite catalyst composition has a size from 2 µm to 500 µm or from 20 µm to 500 µm.

It should also be recognized that many potential solvents and many potential organic additives could be used to form the requisite solutions, slurries, or suspensions. In one aspect, water, optionally in combination with a variety of polar organic solvents, acids, or bases, or a mixture thereof could be used to form the requisite solutions, slurries, or solutions.

In one aspect of the methods of making the composite catalysts, the support material is dried prior to being mixed with the metal. Furthermore, in many embodiments, the steps of the method include further baking the composite catalyst composition. The temperatures employed in the baking step can vary widely, up to 600° C., as it is desirable that the catalyst composition is stable at least 600° C.

4. Methods for Oxidizing Alkanes with Oxygen or Air and a Supported Catalyst Composition Also disclosed herein are methods for oxidizing a $C_2$-$C_{12}$ alkane comprising, contacting the $C_2$-$C_{12}$ alkane with a catalyst composition comprising a support material and a mixed metal composition comprising metals in the molar ratios described by the formula

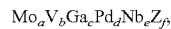

$$Mo_aV_bGa_cPd_dNb_eZ_f,$$

wherein a is 1,
wherein b is from 0.01 to 0.9,
wherein c is greater than 0 to 0.2,
wherein d is from 0.0000001 to 0.2,
wherein e is greater than 0 to 0.2,
wherein Z comprises La, Te, Ge, Zn, Si, In, or W, or a mixture thereof,
wherein f is greater than 0 to 0.5, and
wherein the support material is neutral or oxidative.

It should be understood that the descriptions of the various catalyst components and relevant numerical ratios described above in connection with the composite catalysts themselves can be and/or are applicable in connection with the methods of oxidizing alkanes described here.

In one aspect, the method further comprises contacting the $C_2$-$C_{12}$ alkane and/or the catalyst composition with a stream comprising oxygen and/or air.

It should be understood that the descriptions of the various catalyst components and relevant numerical ratios described above in connection with the composite catalysts themselves can be and/or are applicable in connection with the methods of oxidizing alkanes described here.

The catalytic methods described here relate to methods for the catalytic oxidation of $C_2$-$C_{12}$ alkanes with oxygen or air in the presence of a composite catalyst as described above. Any $C_2$-$C_{12}$ alkane that can be vaporized and mixed with oxygen or air in a non-explosive composition (which may contain a carrier gas diluent) can be used in the method, to produce the corresponding olefins (comprising carbon-carbon double bonds, especially propylene, or α,β-unsaturated carboxylic acids, such as acrylic acid). Examples of suitable alkanes include ethane, propane, and various isomers of $C_4$-$C_{12}$ alkanes such as butanes, pentanes, hexanes, heptanes, octanes, nonanes, decanes, unadecanes, and dodecanes. In one aspect, the $C_2$-$C_{12}$ alkanes comprise propane. In another aspect, the $C_2$-$C_{12}$ alkanes comprise $C_2$-$C_6$ alkanes. In yet another aspect, the $C_2$-$C_{12}$ alkanes comprise $C_2$-$C_4$ alkanes. In one aspect, propane is employed in the method, in order to produce desirable products like acrylic acid and/or propylene.

In one aspect of the methods, oxidation of a $C_2$-$C_{12}$ alkane produces a product molecule comprising a carboxylic acid, or a product molecule comprising a carbon-carbon double bond. In one aspect of the methods, the oxidation produces a molecule comprising a carboxylic acid and a carbon-carbon double bond.

The catalytic methods of the invention typically pass feed stream comprising a mixture of a vaporized alkane such as propylene, oxygen gas or air, or air supplemented with additional oxygen, and an optional diluent or carrier gas, and contact that feed stream with the composite catalyst at a suitable elevated temperature and pressure, by flowing the vapor feed stream into and over the supported catalyst.

The catalyst can be contained within any suitable reactor vessel, in a fixed bed, fluidized bed, or any of the many other arrangements known to those skilled in the catalytic arts.

The feed stream used as the source of the alkane (especially propane) can be a gas stream which contains at least three volume percent of the alkanes (often propane or a mixture of propylene/propane), and often contains less than thirty volume percent of alkane. The gas stream can also contain major amounts, more than five volume percent, of diluents such as nitrogen/argon, carbon dioxide, and water in the form of steam. In many embodiments, the reaction mixture generally contains, per one mole of propane, from 0.01 to 2.0 moles of molecular oxygen, either as pure oxygen or in the form of air, and from zero to 4.0 moles of water in the form of steam. The ratio of propane to oxygen varies with the desired conversion of propane and the selectivity of the catalyst, but generally is in the range of 1/5-5/1. The ratio of propane to diluents can be in the range of 1/5-1/1. Other gases may be used as reaction diluents or heat moderators such as helium, nitrogen and carbon dioxide.

Suitable temperatures for the contacting step can occur between 150° C. and 450° C., or between 280° C. and 310° C. It has been unexpectedly discovered that by supporting the active metal oxide phases described above on neutral or oxidative supports, the methods of oxidizing hydrocarbons can be conducted at unexpectedly low temperatures. Accordingly, in one aspect of the methods, contacting occurs below 295° C. In one aspect, contacting occurs at 280° C., or at 290° C. The methods of oxidizing hydrocarbons described herein can be carried out at higher temperatures. Accordingly, in another aspect, contacting occurs at and/or below 305° C.

Suitable pressures for the contacting step often occur at a pressure from 1 to 50 bar. The reaction pressure may be initially provided by the feed of the gaseous reactants and optional diluents, and after the reaction has commenced may be maintained by the use of a suitable back-pressure controller placed on the reactor outlet stream. The liquid products of the reaction can be separated from the unreacted feed hydrocarbons by condensation or scrubbing, and usually by water or dilute acid in the case of carboxylic acids such as acrylic acid.

The contacting of the feed stream with the composite catalyst is typically carried out with a contact time between the feed stream and the catalyst from 0.01 second to 100 seconds, or from 0.1 second to 10 seconds; the contact time is defined as the ratio between the apparent volume of the catalyst bed and the volume of the gaseous reaction mixture feed to the catalyst bed under the given reaction conditions in a unit of time.

The contacting of the feed stream with the composite catalyst is typically carried out at a space hourly velocity from 50 to 50,000 hr$^{-1}$, or from 100 to 10,000 hr$^{-1}$ or from 200 to 3,000 hr$^{-1}$. The space velocity is calculated by determining the total reactor outlet gas equivalent in liters of the total effluent evolved over a period of one hour divided by the liters of catalyst in the reactor. The room temperature volume is converted to the volume at 0° C. at 1 bar.

One advantage of the catalyst systems of the invention is the high yield of acrylic acid production achieved. In one aspect, the oxidation can provide at least a 30% yield, or at least a 50% yield, or at least a 70% yield of acrylic acid. In one aspect, less than 1% propylene is formed using the composite catalyst and methods of the invention.

In one aspect, the selectivity of conversion to acrylic acid is at least 50% per single pass through the composite catalyst composition. In another aspect, no detectable propylene is formed as a by-product.

One benefit of using the disclosed composite catalysts compositions are high rates of oxidation of alkanes. In one aspect, the space time yield (STY) for oxidation of propane to acrylic acid plus propylene is at least 20% higher relative to a base reference catalyst. In one aspect, the STY for oxidation of propane to acrylic acid plus propylene is at least 30% higher relative to a base reference catalyst. In another aspect, the STY for oxidation of propane to acrylic acid plus propylene is at least 40% higher relative to a reference base catalyst.

In one aspect, the catalyst composition is at least 10% more effective in oxidizing propane to acrylic acid and propylene than an unsupported catalyst composition. In one aspect, the catalyst composition is at least 20% more effective in oxidizing propane to acrylic acid and propylene than an unsupported catalyst composition. In one aspect, the catalyst composition is at least 30% more effective in oxidizing propane to acrylic acid and propylene than an unsupported catalyst composition.

The process is generally carried out in a single stage with all the oxygen and reactants being supplied as a single feed with non-reacted initial reactants being recycled. However, multiple stage addition of oxygen or hydrocarbon to the reactor can be used and/or recycling of un-reacted gases with purge mode can be applied to improve the overall productivity and/or yield of the desired products.

5. Aspects

In view of the described catalyst compositions and methods and variations thereof, herein below are described certain more particularly described aspects. These particularly recited aspects should not however be interpreted to have any limiting effect on any different claims containing different or more general teachings described herein, or that the "aspects" are somehow limited in some way other than the inherent meanings of the language and formulas literally used therein.

Aspect 1: A catalyst composition comprising a support material and a mixed metal composition comprising metals in the molar ratios described by the formula $Mo_aV_bGa_cPd_dNb_eZ_f$, wherein a is 1,
wherein b is from 0.01 to 0.9,
wherein c is from than 0 to 0.2,
wherein d is from 0.0000001 to 0.2,
wherein e is greater than 0 to 0.2,
wherein Z comprises La, Te, Ge, Zn, Si, In, or W, or a mixture thereof, and
wherein f is greater than 0 to 0.5,
wherein the support material is neutral or oxidative.

Aspect 2: The catalyst composition of aspect 1, wherein the support material comprises $Al_2O_3$, $SiO_2$, $CeO_2$, $TiO_2$, or $ZrO_2$, or a mixture thereof.

Aspect 3: The catalyst composition of any one of aspects 1 or 2, wherein the support material comprises $CeO_2$.

Aspect 4: The catalyst composition of any one of aspects 1-3, wherein the support material comprises acetate-$SiO_2$, low surface area $TiO_2$, high surface area $TiO_2$, acetate-$Al_2O_3$, acetate-$ZrO_2$, or actetate-$CeO_2$, or a mixture thereof.

Aspect 5: The catalyst composition of any one of aspects 1-4, wherein the support material is oxidative Aspect 6: The catalyst composition of any one of aspects 1-4, wherein the support material is neutral.

Aspect 7: The catalyst composition of any one of aspects 1-6, wherein the support material is a microporous or mesoporous support material.

Aspect 8: The catalyst composition of any one of aspects 1-7, wherein the catalyst composition has a particle diameter size from 20 μm to 500 μm.

Aspect 9: The catalyst composition of any one of aspects 1-8, wherein Z comprises Te.

Aspect 10: The catalyst composition of any one of aspects 1-9, wherein the catalyst composition is stable to at least 600° C.

Aspect 11: The catalyst composition of any one of aspects 1-10, wherein the catalyst composition is at least 10% more effective in oxidizing propane to acrylic acid and propylene than a corresponding unsupported catalyst composition.

Aspect 12: The catalyst composition of any one of aspects 1-10, wherein the catalyst composition is at least 20% more effective in oxidizing propane to acrylic acid and propylene than a corresponding unsupported catalyst composition.

Aspect 13: The catalyst composition of any one of aspects 1-10, wherein the catalyst composition is at least 30% more effective in oxidizing propane to acrylic acid and propylene than a corresponding unsupported catalyst composition.

Aspect 14: The catalyst composition of any one of aspects 1-13, wherein the support material does not comprise a metal.

Aspect 15: The catalyst composition of any one of aspects 1-13, wherein the support material does not comprise a metal comprising B, La, Mn, Sb, Ti, Zr, La, Fe, Cs, Au, or Ce.

Aspect 16: A method of oxidizing a $C_2$-$C_{12}$ alkane comprising, contacting the $C_2$-$C_{12}$ alkane with an oxygen containing stream and the catalyst composition of any one of aspects 1-15, thereby oxidizing the $C_2$-$C_{12}$ alkane.

Aspect 17: The method of aspect 16, wherein the $C_2$-$C_{12}$ alkane is propane.

Aspect 18: The method of aspects 16 or 17, wherein the oxidation produces an α,β-unsaturated carboxylic acid.

Aspect 19: The method of any one of aspects 16-18, wherein the oxidation produces acrylic acid.

Aspect 20: The method of any one of aspects 16-19, wherein the oxidation produces an olefin.

Aspect 21: The method of any one of aspects 16-20, wherein the oxidation produces propylene.

Aspect 22: The method of any one of aspects 16-21, wherein the oxidation produces acrylic acid and propylene.

Aspect 23: The method of any one of aspects 16-22, wherein the oxidation produces a molecule comprising a carboxylic acid.

Aspect 24: The method of any one of aspects 16-23, wherein the oxidation produces a molecule comprising a carbon-carbon double bond.

Aspect 25: The method of any one of aspects 16-24, wherein the oxidation produces a molecule comprising a carboxylic acid and a carbon-carbon double bond.

Aspect 26: The method of any one of aspects 16-25, wherein the oxidation is at least 10% more effective in oxidizing the $C_2$-$C_{12}$ alkane than a corresponding unsupported catalyst composition.

Aspect 27: The method of any one of aspects 16-25, wherein the oxidation is at least 20% more effective in oxidizing the $C_2$-$C_{12}$ alkane than a corresponding unsupported catalyst composition.

Aspect 28: The method of any one of aspects 16-25, wherein the oxidation is at least 30% more effective in oxidizing the $C_2$-$C_{12}$ alkane than a corresponding unsupported catalyst composition Aspect 29: A method of making a catalyst composition comprising the step of: a) mixing a support material with an active phase, thereby forming a catalyst composition, wherein the support material is neutral or oxidative, thereby forming a catalyst composition.

Aspect 30: The method of aspect 29, wherein the catalyst composition is the catalyst composition of any one of aspects 1-15.

Aspect 31: The method of aspects 29 or 30, wherein the support material is dried prior to being mixed with the active phase.

Aspect 32: The method of any one of aspects 29-31, wherein the method further comprises baking the catalyst composition.

Aspect 33: The method of any one of aspects 29-32, wherein the method further comprises physically modifying the catalyst composition into particles having a diameter size of 20 μm to 500 μm.

EXAMPLES

The following examples are put forth so as to provide those of ordinary skill in the art with a complete disclosure and description of how the compounds, compositions, articles, devices, and/or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

1. Example 1: Preparation of Unsupported Active Oxidation Catalyst—$Mo_1V_{0.398}Ga_{1.0E-05}$ $Pd_{1.90E-04}Nb_{0.125}Te_{0.23}$ An example of the mixed metal composition $Mo_aV_b$-$Ga_cPd_dNb_eX_f$ catalysts for propane oxidation described in U.S. Pat. No. 6,160,162 was prepared by the methods disclosed in that patent, and detailed herein. The specific catalyst prepared in this example is $Mo_1V_{0.398}Ga_{1.0E-05}Pd_{1.90E-04}Nb_{0.125}Te_{0.23}$. Ammonium metavanadate (Aldrich Chemicals, Assay=99.0%) in the amount of 7.6 grams was added to 80 ml of distilled water and heated to 90° C. with stirring. 3.4 grams of niobium oxide (80% $Nb_2O_5$), 28 grams of oxalic acid, and 28.8 g ammonium paramolybdate tetra hydrate (Aldrich Chemicals A.C.S.-12054-85-2) were added to the vanadate solution to make a gel mixture. The required amount of palladium followed by telluric acid and gallium oxide were added slowly to gel mixture. The gel mixture was stirred vigorously to achieve a homogeneous gel mixture which was then dried slowly to incipient dryness with continuous stirring. The resulting solid was put in a China dish and dried additionally in an oven at 120° C. The dried material was cooled to room temperature and placed in a furnace where the catalyst was calcined at 300 to 600° C. for 4 to 16 hours.

The unsupported mixed metal composition catalyst thus prepared comprised metal atoms in the following molar ratios: $Mo_1V_{0.398}Ga_{1.0E-05}Pd_{1.90E-04}Nb_{0.125}Te_{0.23}$. The catalyst in 40/60 mesh size was tested using a feed mixture containing propane: oxygen: nitrogen. The reaction product showed the following results: Propane Conversion 12%; Acrylic acid selectivity 60%; Propylene selectivity 10%; Acetic acid selectivity 10%; COx selectivity 20%. The STY for the combination of Acrylic acid and propylene are considered a reference (or base line) for the rates from the subsequent Examples below.

2. Example 2—Oxidation Catalyst Supported on Acetate-$SiO_2$

The mixed metal composition active catalyst of Example 1 was crushed to a powder of <100 microns and used without further drying. $SiO_2$ (silica) having a surface area of 390 m²/g and 1.1 ml/g pore volume, was dried overnight at 120° C. (5° C./min heating rate).

An ammonium acetate stock solution was prepared by weighing 2.4936 g of ammonium acetate and diluting it to 50 ml in a volumetric flask. To 2.00 g of the silica support was weighed and 10 ml of the ammonium acetate solution was added to the support. The modified support was dried at 120° C. (5° C./min) for 8 hours.

0.45 g the acetate modified $SiO_2$ and 50 mg of the active phase were mixed with 500 µl water and placed in a small metal holder. Two small steel balls were used to grind the mixture in order to get a homogeneous slurry. The mixture was shaken in the ball mill for 30 minutes at 25 Hz. After shaking, the slurry was dried for 8 hours at 110° C. (5° C./min heating rate). 0.44 g material was obtained. After drying, the final material was crushed and sieved to a particle size of 38-425 microns, and tested for propane oxidation under standard conditions described herein.

3. Example 3—Oxidation Catalyst Supported on Low Surface Area Titania (LSA $TiO_2$)

The mixed metal composition active catalyst of Example 1 was crushed to a powder of <100 microns and used without further drying. $TiO_2$ having a surface area of 9.4 m²/g was dried overnight at 120° C. (5° C./min heating rate).

0.45 g $TiO_2$ and 50 mg of the active catalyst of Example 1 were mixed with 500 µl water and placed in a small metal holder. Two small steel balls were used to grind the mixture in order to get a homogeneous slurry. The mixture was shaken in the ball mill for 30 minutes at 25 Hz. After shaking, the slurry was dried for 8 hours at 110° C. (5° C./min heating rate). After drying, the final material was crushed and sieved to a particle size of 38-425 microns, and tested for propane oxidation under standard conditions described herein.

4. Example 4—Oxidation Catalyst Supported on High Surface Area Titania (HSA $TiO_2$)

The mixed metal composition active catalyst of Example 1 was crushed to a powder of <100 microns and used without further drying. $TiO_2$ having a surface area of 132 m/g and pore volume of 0.64 ml/g was dried overnight at 120° C. (5° C./min heating rate).

0.45 g $TiO_2$ and 50 mg of the active catalyst of Example 1 were mixed with 500 µl water and placed in a small metal holder. Two small steel balls were used to grind the mixture in order to get a homogeneous slurry. The mixture was shaken in the ball mill for 30 minutes at 25 Hz. After shaking, the slurry was dried for 8 hours at 110° C. (5° C./min heating rate). After drying, the final HSA $TiO_2$ material was crushed and sieved to a particle size of 38-425 microns, and tested for propane oxidation under standard conditions described herein.

5. Example 5—Oxidation Catalyst Supported on $SiO_2$—$Al_2O_3$

The mixed metal composition active catalyst of Example 1 was crushed to a powder of <100 microns and used without further drying. Aluminosilicate ($Al_2O_3$—$SiO_2$) having a surface area of 607 m²/g and pore volume on 0.8 ml/g was dried overnight at 120° C. (5° C./min heating rate).

0.45 g $Al_2O_3$—$SiO_2$ and 50 mg of the catalyst of Example 1 were mixed with 500 µL water and placed in a small metal holder. Two small steel balls were used to grind the mixture in order to get a homogeneous slurry. The mixture was shaken in the ball mill for 30 minutes at 25 Hz. After shaking, the slurry was dried for 8 hours at 110° C. (5° C./min heating rate). After drying, the final material was crushed and sieved to a particle size of 38-425 microns, and tested for propane oxidation under standard conditions described herein.

6. Example 6—Oxidation Catalyst Supported on Aluminum Phosphate ($AlPO_4$)

The mixed metal composition active catalyst of Example 1 was crushed to a powder of <100 microns and used without further drying. Aluminophoshate ($AlPO_4$) was dried overnight at 120° C. (5° C./min heating rate).

0.45 g $AlPO_4$ and 50 mg of the catalyst of Example 1 were mixed with 500 µL water and placed in a small metal holder. Two small steel balls were used to grind the mixture in order to get a homogeneous slurry. The mixture was shaken in the ball mill for 30 minutes at 25 Hz. After shaking, the slurry was dried for 8 hours at 110° C. (5° C./min heating rate). After drying, the final material was crushed and sieved to a particle size of 38-425 microns, and tested for propane oxidation under standard conditions described herein.

7. Example 7—Oxidation Catalyst Supported on $H_3PO_4$ Modified Alumina ($H_3PO_4$—$Al_2O_3$)

The mixed metal composition active catalyst of Example 1 was crushed to a powder of <100 microns and used without further drying. α-Al$_2$O$_3$ having a surface area of 0.75 m$^2$/g and 0.53 ml/g pore volume was dried overnight at 120° C. (5° C./min heating rate). A phosphoric acid stock solution was prepared by weighing 1.25 g H$_3$PO$_4$ and diluting it to 25 ml in a volumetric flask. 2.00 g of the alumina support was weighed in and 10 mL of the H$_3$PO$_4$ solution was added to the alumina support. The modified support was dried at 120° C. (5° C./min) for 8 hours.

0.45 g of the modified α-Al$_2$O$_3$ and 50 mg of the active catalyst of Example 1 was mixed with 500 μl water and placed in a small metal holder. Two small steel balls were used to grind the mixture in order to get a homogeneous slurry. The mixture was shaken in the ball mill for 30 minutes at 25 Hz. After shaking, the slurry was dried for 8 hours at 110° C. (5° C./min heating rate). 0.44 g of material was obtained. After drying, the final material was crushed and sieved to a particle size of 38-425 microns, and tested for propane oxidation under standard conditions described herein.

8. Example 8—Oxidation Catalyst Supported on H$_3$PO$_4$ Modified Silica (H$_3$PO$_4$—SiO$_2$)

The mixed metal composition active catalyst of Example 1 was crushed to a powder of <100 microns and used without further drying. SiO$_2$ having a surface area of 390 m$^2$/g and 1.1 ml/g pore volume was dried overnight at 120° C. (5° C./min heating rate). A phosphoric acid stock solution was prepared by weighing 1.25 g H$_3$PO$_4$ and diluting it to 25 ml in a volumetric flask. 2.00 g of the silica support was weighed in and 10 mL of the H$_3$PO$_4$ solution was added to the silica support. The modified support was dried at 120° C. (5° C./min) for 8 hours.

0.45 g of the H$_3$PO$_4$ modified SiO$_2$ and 50 mg of the active catalyst of Example 1 was mixed with 500 μl water and placed in a small metal holder. Two small steel balls were used to grind the mixture in order to get a homogeneous slurry. The mixture was shaken in the ball mill for 30 minutes at 25 Hz. After shaking, the slurry was dried for 8 hours at 110° C. (5° C./min heating rate). 0.44 g material was obtained. After drying, the final material was crushed and sieved to a particle size of 38-425 microns, and tested for propane oxidation under standard conditions described herein.

9. Example 9—Oxidation Catalyst Supported on Alumina (Al$_2$O$_3$)

The mixed metal composition active catalyst of Example 1 was crushed to a powder of <100 microns and used without further drying. α-Al$_2$O$_3$ having a surface area of 0.75 m$^2$/g and 0.53 ml/g pore volume was dried overnight at 120° C. (5° C./min heating rate).

0.45 g of the unmodified α-Al$_2$O$_3$ and 50 mg of the active catalyst of Example 1 was mixed with 500 μl water and placed in a small metal holder. Two small steel balls were used to grind the mixture in order to get a homogeneous slurry. The mixture was shaken in the ball mill for 30 minutes at 25 Hz. After shaking, the slurry was dried for 8 hours at 110° C. (5° C./min heating rate). 0.44 g of material was obtained. After drying, the final material was crushed and sieved to a particle size of 38-425 microns, and tested for propane oxidation under standard conditions described herein.

10. Example 10—Oxidation Catalyst Supported on Silica (SiO$_2$)

The mixed metal composition active catalyst of Example 1 was crushed to a powder of <100 microns and used without further drying. SiO$_2$ having a surface area of 390 m$^2$/g, and 1.1 ml/g pore volume, was dried overnight at 120° C. (5° C./min heating rate).

0.45 g SiO$_2$ and 50 mg of the active catalyst of Example 1 was mixed with 500 μl water and placed in a small metal holder. Two small steel balls were used to grind the mixture in order to get a homogeneous slurry. The mixture was shaken in the ball mill for 30 minutes at 25 Hz. After shaking, the slurry was dried for 8 hours at 110° C. (5° C./min heating rate). After drying, the final material was crushed and sieved to a particle size of 38-425 microns, and tested for propane oxidation under standard conditions described herein.

11. Example 11—Oxidation Catalyst Supported on Zirconia (ZrO$_2$)

The mixed metal composition active catalyst of Example 1 was crushed to a powder of <100 microns and used without further drying. ZrO$_2$ having a surface area of 107 m$^2$/g, and 0.3 mL/g pore volume, was dried overnight at 120° C. (5° C./min heating rate).

0.45 g ZrO$_2$ and 50 mg of the active catalyst of Example 1 were mixed with 500 μl water and placed in a small metal holder. Two small steel balls were used to grind the mixture in order to get a homogeneous slurry. The mixture was shaken in the ball mill for 30 minutes at 25 Hz. After shaking, the slurry was dried for 8 hours at 110° C. (5° C./min heating rate). 0.44 g material was obtained. After drying, the final material was crushed and sieved to a particle size of 38-425 microns, and tested for propane oxidation under standard conditions described herein.

12. Example 12—Oxidation Catalyst Supported on Ceria (CeO$_2$)

The mixed metal composition active catalyst of Example 1 was crushed to a powder of <100 microns and used without further drying. CeO$_2$ having a surface area of 130 m$^2$/g, and 0.24 ml/g pore volume, was dried overnight at 120° C. (5° C./min heating rate).

0.45 g CeO$_2$ and 50 mg of the active phase were mixed with 500 μl water and placed in a small metal holder. Two small steel balls were used to grind the mixture in order to get a homogeneous slurry. The mixture was shaken in the ball mill for 30 minutes at 25 Hz. After shaking, the slurry was dried for 8 hours at 110° C. (5° C./min heating rate). 0.43 g of solid catalyst material was obtained. After drying, the final material was crushed and sieved to a particle size of 38-425 microns, and tested for propane oxidation under standard conditions described herein.

13. Example 13—Oxidation Catalyst Supported on Acetate Modified Alumina (Acetate-Al$_2$O$_3$)

The mixed metal composition active catalyst of Example 1 was crushed to a powder of <100 microns and used without further drying. α-Al$_2$O$_3$ having a surface area of 0.75 m$^2$/g and 0.53 ml/g pore volume was dried overnight at 120° C. (5° C./min heating rate).

0.45 g of the modified α-Al$_2$O$_3$ and 50 mg of the active phase were mixed with 500 μl water and placed in a small metal holder. Two small steel-balls were used to grind the mixture in order to get a homogeneous slurry. The mixture was shaken in the ball mill for 30 minutes at 25 Hz. After shaking, the slurry was dried for 8 hours at 110° C. (5° C./min heating rate). 0.44 g material was obtained. After drying, the final material was crushed and sieved to a particle size of 38-425 microns, and tested for propane oxidation under standard conditions described herein.

14. Catalyst Testing Rate Data

All the specific catalysts described in Example 1-13 were tested for catalyst activity for propane oxidation using a standard procedure described here. Catalyst evaluations were carried out using 0.40-0.60 gram of 38-425 mesh size catalyst samples paced into a stainless steel fixed bed tubular reactor and fed a mixture containing propane:oxygen:nitrogen at a ratio of 71.25:23.75:5 (at a temperature of 290° C. to 305° C., pressure of 15 psig and at space velocity of 1,090 $h^{-1}$).

Reaction products were analyzed on-line by gas chromatography. Oxygen, argon and carbon monoxide were analyzed using a 2.5 mm by 3 mm column of 13.times.molecular sieve. Carbon dioxide, propane and propylene were analyzed using a 2 mm by 3 mm column packed with material sold under the trade name HAYESEP Q®. Liquids products (acrylic acid, acrolein, acetic acid and water) were collected for a certain period in the cold trap and were analyzed using a 2 mm by 3 mm column packed with material sold under the trademark PORAPAK Q® In all cases, the conversion and selectivity calculations were based on the reaction stoichiometry.

The data table below lists the results of experiments that tested the catalysts of Examples 1-13 described above for propane oxidation under the standard conditions also described above. The data in the Table gives the ratio of the observed STY for total production of propylene and acrylic acid for each of the catalysts described in Examples 2-13 as compared to the STY for production of total and acrylic acid for Example 1, which used the unsupported $Mo_1V_{0.398}Ga_{1.0E-05}Pd_{1.90E-05}Nb_{0.125}Te_{0.23}$.

TABLE 1

| | STY of propylene and acrylic acid | | |
|---|---|---|---|
| Example | Type | Support name | Relative STY ratios of Propylene & Acrylic acid |
| 1 | oxide | None | 100 |
| 2 | neutral | Acetate-SiO$_2$ | 128.2 |
| 3 | oxidative | LSA TiO$_2$ | 124.8 |
| 4 | oxidative | HSA TiO$_2$ | 110.4 |
| 5 | acidic | SiO$_2$—Al$_2$O$_3$ | 81.5 |
| 6 | acidic | AlPO$_4$ | 36.4 |
| 7 | acidic | H$_3$PO$_4$—Al$_2$O$_3$ | 78 |
| 8 | acidic | H$_3$PO$_4$—SiO$_2$ | 71.2 |
| 9 | neutral | Al$_2$O$_3$ | 121.9 |
| 10 | neutral | SiO$_2$ | 136.2 |
| 11 | oxidative | ZrO$_2$ | 115.8 |
| 12 | oxidative | CeO$_2$ | 114 |
| 13 | neutral | Acetate-Al$_2$O$_3$ | 112.5 |

The results from the Table are bar graphed in FIG. 1, which presents the results obtained at 290° C.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A catalyst composition comprising a support material and a mixed metal composition comprising metals in the molar ratios described by the formula $$Mo_aV_bGa_cPd_dNb_eZ_f,$$

wherein a is 1,
wherein b is from 0.01 to 0.9,
wherein c is from greater than 0 to 0.2,
wherein d is from 0.0000001 to 0.2,
wherein e is greater than 0 to 0.2,
wherein Z comprises La, Te, Ge, Zn, Si, In, or W, or a mixture thereof, and
wherein f is greater than 0 to 0.5,
wherein the support material is neutral or oxidative,
wherein the support material comprises acetate-SiO$_2$, acetate-Al$_2$O$_3$, acetate-ZrO$_2$, or actetate-CeO$_2$, or a mixture thereof.

2. The catalyst composition of claim 1, wherein the support material comprises acetate-SiO$_2$.

3. The catalyst composition of claim 1, wherein the support material comprises actetate-CeO$_2$.

4. The catalyst composition of claim 1, wherein the support material comprises acetate-ZrO$_2$.

5. The catalyst composition of claim 1, wherein the support material is oxidative.

6. The catalyst composition of claim 1, wherein the support material is neutral.

7. The catalyst composition of claim 1, wherein the support material is a microporous or mesoporous support material.

8. The catalyst composition of claim 1, wherein the catalyst composition has a particle diameter size from 20 μm to 500 μm.

9. The catalyst composition of claim 1, wherein Z comprises Te.

10. The catalyst composition of claim 1, wherein the catalyst composition is stable to at least 600° C.

11. The catalyst composition of claim 1, wherein the catalyst composition is at least 10% more effective in oxidizing propane to acrylic acid and propylene than a corresponding unsupported catalyst composition.

12. The catalyst composition of claim 1, wherein the catalyst composition is at least 20% more effective in oxidizing propane to acrylic acid and propylene than a corresponding unsupported catalyst composition.

13. The catalyst composition of claim 1, wherein the catalyst composition is at least 30% more effective in oxidizing propane to acrylic acid and propylene than a corresponding unsupported catalyst composition.

14. The catalyst composition of claim 1, wherein the support material does not comprise a metal.

15. The catalyst composition of claim 1, wherein the support material does not comprise a metal comprising B, La, Mn, Sb, Ti, Zr, La, Fe, Cs, Au, or Ce.

16. A method of oxidizing a C2-C12 alkane comprising, contacting the C2-C12 alkane with an oxygen containing stream and the catalyst composition of claim 1, thereby oxidizing the C2-C12 alkane.

17. The method of claim 16, wherein the C2-C12 alkane is propane.

18. The method of claim 16, wherein the oxidation produces acrylic acid and propylene.

19. The method of claim 16, wherein the oxidation is at least 30% more effective in oxidizing the C2-C12 alkane than a corresponding unsupported catalyst composition.

20. A method of making the catalyst composition of claim 1 comprising the step of
   a) mixing a support material with an active phase comprising the mixed metal composition of claim 1, thereby forming a catalyst composition, wherein the support material is neutral or oxidative and comprising acetate-$SiO_2$, acetate-$Al_2O_3$, acetate-$ZrO_2$, or actetate-$CeO_2$, or a mixture thereof, thereby forming the catalyst composition of claim 1.

* * * * *